United States Patent [19]

Spragg et al.

[11] Patent Number: 5,045,452
[45] Date of Patent: Sep. 3, 1991

[54] METHOD FOR EVALUATING NEPHROTOXICITY

[75] Inventors: Jocelyn Spragg, Jamaica Plain; K. Frank Austen, Wellsley, both of Mass.

[73] Assignee: Brigham and Women's Hospital, Boston, Mass.

[21] Appl. No.: 259,115

[22] Filed: Sep. 2, 1988

[51] Int. Cl.$^5$ ............................................. G01N 33/535
[52] U.S. Cl. ..................................... 435/7.4; 435/7.6; 435/24; 436/548
[58] Field of Search ....................... 435/7, 24, 7.4, 7.6; 424/9; 436/548

[56] References Cited

FOREIGN PATENT DOCUMENTS 210029 1/1987 European Pat. Off. ............ 530/387

OTHER PUBLICATIONS

Spragg et al., "Urinary Kallikrein Excretion: An Index of the Nephrotoxic Response to Cyclosporine in Rheumatoid Arthritis", Clin. Res., 34 (1986) 730A.
Chmielnicka et al., "Arginase and Kallikrein Activities as Biochemical Indexes of Occupational Exposure", Chem. Abstracts, 95 (1981), Abstract #55780w.
Iannaconne et al., "Urinary Kallikrein in Lead-Exposed Workers", Chem. Abstracts, 89 (1978), Abstract #11323w.
Spragg et al., "Kallikrein Excretion in Renal Transplant Recipients and in Uninephectomized Donors", Kidney International, 28 (1985), 75-81.
Silver et al., "Active Site Radioimmunoassay for Human Urokallikrein and Demonstration by Radioimmunoassay of a Latent Form of the Enzyme", J. Immunol., 124 (1980), 1551-1555.
Woodley et al., "Specific Identification of Tissue Kallkirein in Exocrine Tissues and in Cell-Free Translation Products with Monoclonal Antibodies", Biochem. J., 231 (1985), 721-728.
Lauwerys et al., "Early Detection of the Pephrotoxic Effects of Industrial Chemicals: State of the Art and Future Prospects", Am. J. Indust. Med., 11 (1987).
Levinsky et al., Biochemical Pharmacology 38:2491-2595 (1979).
Koolen et al., Transplantation 37(5):471-474 (1984).

Primary Examiner—Christine Nucker
Attorney, Agent, or Firm—Sterne, Kessler, Goldstein & Fox

[57] ABSTRACT

A method for evaluating cyclosporine-related nephrotoxicity in a patient receiving cyclosporine therapy is disclosed. The method comprises measuring urine kallikrein content utilizing radioimmunoassay specific for human urine kallikrein. The value obtained is compared then to a pre-treatment value of urine kallikrein levels.

Also disclosed is a means for predicting susceptibility to cyclosporine-related nephrotoxicity. Potential cyclosporine therapy patients are evaluated according to their baseline (pre-treatment) urinary kallikrein levels. Low initial levels of urine kallikrein are predictive of susceptibility to cyclosporine-related nephrotoxicity.

Also disclosed is a method for monitoring cyclosporine-related nephrotoxicity during the course of cyclosporine treatment. Decreased urinary kallikrein indicates that cyclosporine administration should be decreased or terminated. Increased urinary kallikrein indicates that cyclosporine administration may be increased or maintained. Stable urinary kallikrein indicates that cyclosporine administration may be maintained. Monitoring kallikrein according to the present invention provides an early and sensitive means of predicting cyclosporine-related nephrotoxicity during cyclosporine treatment. Episodic decreases in urinary kallikrein precede increases in serum creatinine by one to four months.

24 Claims, 2 Drawing Sheets

METHOD FOR EVALUATING NEPHROTOXICITY

BACKGROUND OF THE INVENTION

1. Field of the Invention

This invention is directed to the discovery that both the nephrotoxic effect of in-progress nephrotoxic therapy on an individual as well as the potential for nephrotoxic effect of contemplated therapy on a given individual can be evaluated as a function of urine kallikrein content.

In the first instance, the urine kallikrein level of a patient receiving such therapy is monitored and compared to the patient's baseline (pretherapy) urine kallikrein level. In the second instance, low baseline urine kallikrein is predictive of patients who are at greater risk for developing nephrotoxic reaction to therapeutic compositions, such as those comprising cyclosporine.

2. Description of the Background Art

Cyclosporine is a cyclic, nonwater-soluble, highly nonpolar molecule composed of eleven amino-acids. The compound is a promising immunosuppressive agent which is derived from soil fungus (Calne et al., Transplant Proc. 13:349–358, (1981); Ferguson et al., Surgery, 92:175–182, (1982); Starzl et al., Gynecol. Obstet., 151:17–26, (1980)). The drug is now widely used for prolonging the function of various transplanted organs. Its immunosuppressive effects selectively inhibit T-cell function, allowing survival of allografts without myelosuppression, i.e. heart transplants, Myers et al., N. Eng. J. Med. 311:699 (1984).

In addition to its use in allograft recipients, recent clinical trials have been or are being undertaken to examine the efficacy of cyclosporine in the treatment of a wide variety of autoimmune diseases, including polymyositis, systemic lupus erythematosus, rheumatoid arthritis, and early insulin dependent diabetes (see relevant chapters in: Cyclosporine in Autoimmune Diseases, ed. Schindler, R., Springer-Verlag, Berlin (1985), particularly von Graffenreid, B. et al., pp. 59–73).

Cyclosporine is a lipophilic molecule with a molecular weight of 1202 daltons. When the drug is dissolved in olive oil or a special solution prepared by the manufacturer, bioavailability and absorption are maximized. The drug readily binds to plasma proteins and has a terminal half-time of 24 hours. It is highly metabolized in the liver, with biliary excretion being the major route of elimination (Beveridge, T., Cyclosporine A:, Proceedings of the International Symposium, Cambridge, White, D. J., ed., pages 35–44 (1982)). In addition to its immunosuppressive characteristics, the drug also has interesting anti-schistosome and anti-malarial activities (Kolata, Science (Washington, D.C.) 221:40–42, (1983); Sanches et al., First Int'l. Montreux Conf. on Biol. Rhythms and Medications, Montreux, Switzerland, Mar. 26–30, 1984. Pergamon Press, Oxford, (in press).

In spite of its great promise as an immunosuppressive, however, its use is somewhat limited, both by its association with infection and also because of hepatic and renal toxicities (Ryffel, OL 27-400: "Summary of Toxicity Data," Sandoz, Basel, Switzerland, (1981)).

Clinical use of cyclosporine is associated with reversible, dose-related increases in blood urea nitrogen (BUN) and serum creatinine levels and depression of creatinine clearance. Some nephrotoxicity is reported to occur in almost 80% of renal transplant patients using cyclosporine (Kahan, B. D., Dial. Transplant., 12:620-30 (1983)). Often the urea nitrogen level is disproportionately increased relative to the serum creatinine level. However, no characteristic changes in the urinary sediment distinguish cyclosporine nephrotoxicity from renal allograft rejection. Thus, the differential diagnosis of rejection in nephrotoxicity largely depends on the presence of associated signs of rejection, such as fever and graft tenderness. Diagnostic difficulties are increased in the early post-transplantation period, when recipients of cadaver allografts are frequently oliguric and dialysis-dependent due to acute tubular necrosis. Renal function in such patients improves with decreasing doses of cyclosporine. (Bennett, W. M. et al., Ann. Int., 99:851–854 (1983)).

In addition, many substances with nephrotoxic potential are present in the environment, particularly in the work place. Lead, mercury, cadmium, and a variety of volatile organic compounds, particularly the halogenated aliphatic hydrocarbons, can produce acute renal disease. The assessment of renal injury based upon serum creatinine or blood urea nitrogen levels is insensitive, these tests demonstrating abnormal findings only when major impairment of renal excretory function has developed. Other measures of renal function, such as creatinine clearance, paraaminohippuric acid clearance, urinary concentrating ability, proteinuria, or glycosuria are, perhaps, somewhat more sensitive, but are technically not satisfactory for use as screening tests. Berndt, W. O., Toxicology of the Kidneys, Hook, J. B., ed., New York: Raven Press, pp. 1–29 (1981); Balazs, T. et al., Toxicol. Appl. Pharmacol., 5:661–674 (1963).

It is known that urinary enzyme analysis provides an extremely sensitive indicator of renal injury. Urinary enzyme levels have been shown to be elevated in a wide spectrum of renal diseases including glomerular and interstitial as well as tubular disease, often prior to the onset of renal failure or even before any abnormality in excretory function is detectable, Price, R. G., Toxicology, 23:99–134 (1982); Maruhn, D., Curr. Probl. Clin. Biochem., 9:135–149 (1979); Piperno, E., supra, pp. 31–55; Sherman, R. L. et al., Arch. Intern. Med., 143:1183–1185 (1983). N-acetyl-beta-D-glucosaminidase, a lysosomal enzyme present in renal tubular cells, has been shown to be an extremely sensitive indicator of early renal injury Well, J. M., Br. Med. J., 3:408–411 (1975); Price, R. G., Curr. Prob. Clin. Biochem., 9:150–163 (1979); Hultberg, B. et al., Clin. Nephrol., 15:33–38 (1981); Kunin, C. M. et al., Pediatrics, 62:751–760 (1978); Viganor, A. et al., Biochem. Med., 25:26–33 (1981); Price, R. G. et al., Clin. Chim. Acta., 27:65–72 (1970); Lockwood, T. D. et al., Toxicol. Appl. Pharmacol., 49:323–336 (1979). Myer, B. R. et al., (Am. J. Med., 76:989–990 (1984)) investigated workers exposed to mercury, lead, or volatile organic compounds and observed elevated urinary acetyl glucosaminidase excretion in these workers. They have proposed this high level of acetyl glucosaminidase as an indication of renal injury.

Kallikrein is an endopeptidase that generates vasoactive polypeptides from kininogens, plasma alpha$_2$-globulin substrates (Werle, E. et al., Substanz. Biochem. Z., 289:217 (1937)). It is secreted as an inactive precursor which can be activated in vitro by trypsin (Spragg, Adv. Exp. Med. Biol., 156A:393 (1983)) or thermolysin (Noda et al., Kidney Int., 27:630–635 (1985)). Human urinary kallikrein (urokallikrein or HUK), when purified on the basis of its kinin-generating activity by conventional chromatographic techniques, has been shown to contain a non-kinin-generating alkaline TAMe esterase which can be separated from urokallikrein by broad range isoelectric focusing or by alkaline polyacrylamide disc gel electrophoreses (ole-MoiYoi, O. et al., *Biochem. Pharmacol.* 26:1893 (1977)). Electrophoretic, antigenic, and immunohistochemical studies have established that urokallikrein and the TAMe esterase represent two distinct renal enzymes (Pinkus, G. S. et al., *J. Histochem. Cytochem.*, Vol. 29, no. 1, 38–44 (1981)). Studies of urokallikrein excretion in physiologic and pathologic circumstances are difficult to interpret utilizing esterolytic assays because of the presence of such nonurokallikrein esterases which cleave the same synthetic substrates (ole-MoiYoi, O. et al., *Biochem. Pharmacol.* 26:1893 (1977); Levinsky, N. G. et al., *Biochem. Pharmacol.*, 28:2491 (1979)). The use of a tri-peptide p-nitroanilide substrate to measure kallikrein levels is also not specific, since damaged kidneys may filter or secrete non-kallikrein enzymes which cleave this substrate (Koolen et al., *Transplantation*, 37:471–474 (1984)).

The observation that trypsin treatment of crude urine or a partially purified fraction of urine increases both the esterase (Pisano, J. J. et al., *Contrib. Nephrol.*, 12:116 (1978)) and kininogenase (Spragg, J., *Adv. Exp. Med. Biol.*, 156A:393–398 (1983)) activities of the sample render invalid the use of functional assays of untreated urine samples to determine total kallikrein synthesis and excretion by the kidney.

Silver, M. R. et al., *J. Immun.*, Vol. 124, No. 4, 1551–1555 (1980) developed a radioimmunoassay specific for the active form of urokallikrein utilizing a monospecific antibody that neutralizes the enzymatic activities of urokallikrein and a radioligand purified so as to maintain the active site. Active kallikrein was measured in urine in the absence of trypsin treatment, and total kallikrein was measured after trypsin treatment. Utilizing these radioimmunoassays, the rate of tissue kallikrein excretion into the urine was examined in renal transplant recipients, in post uninephrectomy kidney donors, and in a normal control population (Spragg., J. et al., *Kidney International*, Vol. 28, 75–81 (1985)). It was observed and reported that kallikrein excretion in uninephrectomized donors and in kidney recipients remained significantly lower than in normal controls. Spragg et al. hypothesized that the reduced kallikrein excretion in postuninephrectomized kidney donors and the even lower excretion in renal allograft recipients suggest that renal kallikrein excretion reflects functional distal tubular mass. Since some of the patients in the Spragg et al. study had received immunosuppressive therapy with cyclosporine, a drug known to have both functional and morphological tubulotoxic effects, it could not be determined whether or not the diminished kallikrein excretion rates in the allograft recipient groups reflected rejection, altered function in a denervated kidney; cyclosporine toxicity or a combination of these factors.

Thus, prior to the present invention, a need had continued to exist for a non-invasive means for evaluating cyclosporine-related nephrotoxicity and a means for predicting potential high-risk cyclosporine therapy patients. In addition, a need has continued to exist for an non-invasive means for evaluating the nephrotoxic effect of other potentially nephrotoxic agents. A need had also continued to exist for a means for distinguishing between nephrotoxicity and allograft rejection in patients being treated with cyclosporine.

SUMMARY OF THE INVENTION

The present inventors first succeeded in correlating urinary kallikrein levels with cyclosporine-related nephrotoxicity. It was thus realized that kallikrein levels are an indication of the nephrotoxicity of cyclosporine and of other potentially nephrotoxic compositions.

In one method of the present invention, total urinary kallikrein levels are measured utilizing a radioimmunoassay for human urokallikrein, said radioimmunoassay comprising a monospecific antibody which has been shown to recognize both the active and trypsin-activatable forms of the enzyme (Pinkus et al., *J. Histochem Cytochem*, 31:1279–1288 (1983)) and a radioligand purified so as to maintain its active site. In this manner, comparison of the rate of urinary kallikrein antigen excretion of the cyclosporine-treated patient with pre-treatment base line levels of urine kallikrein provides a means for evaluating the nephrotoxic effect of the cyclosporine therapy. The same method is applicable to other nephrotoxic agents.

In another method of the present invention, total urinary kallikrein levels are measured as above and compared to the patient's prior kallikrein levels during cyclosporine treatment. In this manner, the nephrotoxic effect of cyclosporine may be monitored. For example, decreases in kallikrein will reflect impaired renal function and indicate that cyclosporine administration should be reduced or terminated. Increases in kallikrein, on the other hand, reflect improved renal function and indicate that cyclosporine administration may be increased or maintained. Steady kallikrein levels indicate that cyclosporine administration may be maintained. The same method is applicable to other nephrotoxic agents.

In yet another method of the present invention, increases in serum creatinine in a patient undergoing therapy with agents which are potentially nephrotoxic may be predicted by measuring kallikrein levels during cyclosporine treatment. It has been found that episodic decreases in kallikrein levels are temporally related to increases in serum creatinine. Thus, kallikrein decreases presage serum creatinine increases by one to four months. This method provides an early and sensitive indicator of renal dysfuction brought about by cyclosporine treatment. The same method is applicable to other nephrotoxic agents.

Similarly, measurement of urinary kallikrein in pre-therapy patients provides a means for predicting potential nephrotoxic response to cyclosporine or other nephrotoxic therapy.

BRIEF DESCRIPTION OF THE DRAWINGS

FIG. 1 is a graphic representation of the effect of cyclosporine on urinary kallikrein (HUK) excretion in patients with rheumatoid arthritis. Drug administration was begun at week 1 and terminated at week 24. Patients represented here had normal or elevated control excretion rates. Means and standard deviations are shown for the weeks completed by all patients. The asterisks in FIG. 1 indicate that the mean for weeks 12 and 24 were significantly different from the base line value ($p<0.01$). Because of the high base line HUK excretion rate of patient 1, her subsequent values were not included in the statistical analysis.

DESCRIPTION OF THE PREFERRED EMBODIMENTS

To determine the effect of cyclosporine administration on total urinary kallikrein antigen excretion in the intact, innervated human kidney, kallikrein excretion was measured in patients with rheumatoid arthritis who were participating in a trial to evaluate the efficacy of cyclosporine therapy.

Because kidney damage may lead to the urinary excretion of enzymes other than kallikrein that are capable of cleaving the frequently used tripeptide p-nitroanilide substrate S-2266 (Koolen, M. I. et al., *Transplantation*, 37:471-474 (1984)), and because urine contains *esterases* other than kallikrein (Levinsky, N. G. et al., supra), the excretion of urokallikrein must be measured utilizing an assay which takes the above into account. A suitable assay is the active site radioimmunoassay of Silver et al, supra. A similar radioimmunoassay to measure total kallikrein antigen without the necessity of trypsin treatment of urine samples employs an antibody which recognizes both active and latent forms of kallikrein and therefore measures total kallikrein directly (Pinkus et al., *J. Histochem. Cytochem.*, 31:1279-1288 (1983)).

THE ASSAY

Preparation and Labeling of Urokallikrein

Human urokallikrein for use in the radioimmunoassay is purified from concentrated fresh pooled human urine, typically by affinity chromatography modified for a batch procedure and by gel filtration. Concentrated urine is incubated with gel. The affinity gel is then washed and the urokallikrein is eluted from the affinity gel and collected. The urokallikrein is further purified, i.e., by gel filtration as described, and the final preparation is purified to homogeneity. Demonstration of homogeneity is by alkaline disc gel electrophoresis, by sodium dodecyl sulfate-polyacrylamide gel electrophoresis (SDS-PAGE), with and without reduction, and by amino terminal analysis. The concentration of the purified urokallikrein is determined, typically by Folin assay or absorbance at A=280. A single preparation of this purified urokallikrein quantitated on the basis of its amino acid content is designated "urokallikrein standard," divided into aliquots, stored at low temperature, i.e. $-70°$ C., and used to prepare all standard curves in the radioimmunoassay.

The purified urokallikrein is then labeled using techniques known to the art. Typical labels include radiolabels, enzyme labels, chemiluminescent labels, fluorescent labels, free radical labels and the like. Radiolabeling is preferred, with a typical labeling of urokallikrein effected as below. $^{125}$I-monoiodo-Bolton-Hunter reagent is mixed with purified urokallikrein and then incubated overnight The reaction mixture is applied to an equilibrated Sephadex G-25 column and filtered, with fractions collected. The $^{125}$I-urokallikrein present in the fraction at the exclusion volume of the Sephadex column is directly applied to an affinity column of aprotinin Sepharose and the effluent repeatedly reapplied. The column is then washed with cold equilibration buffer, and the $^{125}$I-urokallikrein is eluted with an acidic buffer. Fractions are collected in tubes and neutralized. This procedure yields 125I-urokallikrein with a defined specific activity (approximately $6 \times 10^5$ cpm/ug) and this radioligand is divided into aliquots and stored at $-70°$ C.

Performance of the Radioimmunoassay

The monospecific anti-urokallikrein IgG used for the active site specific radioimmunoassay inhibits both the kinin-generating and esterolytic functions of purified urokallikrein in a dose-dependent fashion, thereby indicating specificity for determinants at or near the active site of the enzyme. The monospecific anti-urokallikrein IgG used for the total kallikrein radioimmunoassay does not inhibit the interaction of kallikrein with the small ester substrate (Pinkus et al., *J. Histochem. Cytochem.*, 31:1279-1228 (1983)). IgG fractions of both anti-sera were prepared by chromatography, typically DE-52 cellulose, and filtration, typically Sephadex (ole-MoiYoi et al., *J. Immunol.*, 121:66-71 (1978)). The radioimmunoassay is performed in sodium borate buffer (i.e., 0.1 M) containing gelatin. Portions of a 1/400 dilution of anti-urokallikrein IgG are mixed with crude urine samples or with dilutions of urokallikrein standard in buffer; the final volume of each reaction mixture is made equal with buffer. After the addition of $^{125}$I-urokallikrein, the samples are incubated. Then normal rabbit serum and the IgG fraction of goat anti-rabbit IgG are added to each tube. After incubation, the tubes are centrifuged and the supernatants are removed. The precipitates are resuspended in buffer and centrifuged again. The precipitates and the pooled supernatants from each tube are counted in a gamma-counter to yield bound and free counts, respectively. The assay is calibrated with varying dilutions of urokallikrein standard, each prepared in borate buffer.

In addition to the monospecific antibody described above, it is also within the scope of the present invention to utilize a monoclonal antibody recognizing either the active site as in Silver et al., supra, or total kallikrein as in Pinkus et al., supra. The preparation of such monoclonal antibodies employs techniques known to the art.

An antibody titration curve, developed by using varying doses of anti-urokallikrein IgG and a fixed amount of $^{125}$I-urokallikrein, is dose-related between dilutions of anti-urokallikrein. To prepare a reference curve, varying concentrations of urokallikrein standard (i.e., 0.2 to 3 ng/20 ul) are used in the assay, and the ratios of bound to free counts are plotted as a function of the concentration of urokallikrein standard. The amount of $^{125}$I-urokallikrein used is chosen such that approximately 80% of the bindable counts are precipitated by the 1/400 dilution of anti-urokallikrein IgG used for the radioimmunoassay. Crude urine samples are assayed in duplicate in 5- to 30-ul volumes and bound:free count ratios are used to determine urokallikrein concentrations from the standard curve.

Preparation of Samples for Assay

Urine samples, are immediately placed at 4° C. and are assayed on the day of collection or frozen at $-70°$ C. until they are assayed. When full functional activation of the kallikrein in the urine is desired, urine samples are exposed to insolubilized trypsin. Trypsin-CH-Sepharose 4B is prepared by using activated CH-Sepharose 4B in a modification of the manufacturer's recommended procedure. The activated-CH-Sepharose 4B is washed in a coarse Buchner fritted glass funnel with ice-cold 1 mM HCl, followed by potassium phosphate, pH 5.8. The gel is then transferred to a solution of the same buffer containing trypsin. The unreacted trypsin is separated from the trypsin-CH-Sepharose 4B and the gel is treated with ethanolamine and washed with buffers and stored.

Urine samples are treated with trypsin by mixing insolubilized trypsin with cold urine and incubating at room temperature with shaking. The tubes are then centrifuged and the supernatants are removed and stored until assayed.

The enzymatic activity of urokallikrein is assessed by its ability to generate kinin from heat-inactivated human plasma. Samples of urine, with or without exposure to insolubilized trypsin are incubated with heat-inactivated plasma. The mixtures are immediately assayed for formed kinin on a guinea pig terminal ileum or estrous rat uterus segment. The kinin generated is quantitated by comparison with the contractile response of the tissue to standards of synthetic bradykinin.

Thus it may be seen that the present invention is dependent upon an assay for kallikrein which is sufficiently sensitive to detect changes in levels of excretion of kallikrein while avoiding spurious data resulting from the activity of enzymes other than kallikrein. The assay also avoids spurious data resulting from measurement of other enzyme products (peptide) which may be active in the bioassays. The assay is technically feasible and has the particular advantage that procurement of the assay sample (urine) does not require an invasive procedure.

In practicing one embodiment of the present invention, urinary kallikrein is determined in a patient prior to the inception of cyclosporine therapy. In this manner, the patient's baseline (pre-therapy) level of kallikrein is established. Once the baseline value of the kallikrein excretion is established, this value provides two functions.

In the first instance, subsequent kallikrein excretion level determinations, such determinations made subsequent to the inception of, and during the course of, cyclosporine therapy, may be compared to the baseline level of kallikrein excretion. The comparison then provides a measure of the degree to which the cyclosporine therapy is impacting upon kidney function, i.e., the degree of nephrotoxicity resulting from the cyclosporine therapy.

In the second instance, this baseline value provides a predictive function. Where the baseline level for a particular patient indicates levels of kallikrein excretion which are substantially lower than the average baseline levels for a normal control population, i.e., 113.68±8.39 ng/24 hr. (see Table 2) then one can quite accurately predict that the proposed cyclosporine therapy is contra-indicated.

In practicing another embodiment of the present invention, urinary kallikrein is determined in a patient during the course of cyclosporine therapy. The frequency of urinary kallikrein determinations can be varied to suit the particular needs of the patient in view of the patient's medical history, age, health, etc., and the many other variables affecting such determinations, as is well known to those of skill. Monthly determinations are preferred, but determinations at more or less frequent intervals may be indicated in a particular case.

It has been discovered that decreased kallikrein excretion is temporally related to increased serum creatinine. In particular, decreases in kallikrein have been observed to precede increased serum creatinine by one to four months. Since increased serum creatinine indicates substantial loss of filtering nephrons, decreased kallikrein provides an early and sensitive index of nephrotoxicity.

Thus, according to the present invention a decrease in kallikrein will indicate that cyclosporine administration should be decreased or stopped to avoid damage to the kidneys. Similarly, where kallikrein levels remain stable during the course of cyclosporine therapy, this indicates that renal function is not degenerating. The onset of cyclosporine treatment, of course, often will result in a change in kallikrein levels that reflects the nephrotoxic effect of the drug. Assuming that the treatment level is therapeutically acceptable, however, maintenance of stable kallikrein levels indicates that cyclosporine administration may safely be maintained. Similarly, an increase in kallikrein levels during ongoing cyclosporine treatment suggests improved renal function. This indicates that cyclosporine administration may be increased.

will be appreciated that this embodiment of the present invention does not rely upon comparisons of a patient's kallikrein levels with that patient's pre-treatment baseline levels or with a statistically derived standard baseline level. Instead, the patient's own kallikrein levels are monitored during cyclosporine treatment and compared with prior levels during the same course of treatment. This embodiment of the invention, then, provides a means by which nephrotoxic effect may be predicted at a given cyclosporine dosage, and the dosage adjusted to preclude renal damage. It also provides a means by which the therapist may optimize cyclosporine administration during the treatment of an individual patient, by monitoring that patient's kallikrein levels.

In yet another embodiment of the present invention, decreases in urinary kallikrein provide a means of predicting subsequent increases in serum creatinine. For example, patients receiving chronic cyclosporine therapy at reduced doses (3 mg/kg/day) were observed to experience episodic decreases in kallikrein excretion. Episodes in which kallikrein excretion decreased by 49±15% over a one-month interval preceded any increase in serum creatinine by one to four months (see Table 4).

While the above discussion has focused on evaluating cyclosporine-related nephrotoxicity, the invention has utility for evaluating the nephrotoxic effect of other agents, such as aminoglycoside antibiotics, analgesic drugs, i.e., phenacetin, non-steroidal anti-inflammatory drugs, e.g., aspirin, and environmental contaminants as described above, as well.

Having now generally described the invention, the same will be further described by reference to the following examples, which are provided herein for purposes of illustration only and are not intended to be limiting unless otherwise specified.

EXAMPLE

Materials and Methods

PATIENTS. Ten Caucasian patients (8 women and 2 men) who had not responded to previous therapy with D-pencillamine, gold, or gold salts, who had no evidence of Sjogren's syndrome or of conditions associated with renal dysfunction, and who had no evidence of abnormal renal function as assessed by serum creatinine, BUN, and absence of uncontrolled essential hypertension, were enrolled. Hypertension was defined as a diastolic blood pressure of ≧90 mm Hg and there was no difference between the supine and seated pressures read during each examination. Two patients were 32 and 36 years old and the rest ranged from 50 to 69 (mean=59.4) years (Table 1). Background medications for treatment of associated medical conditions as well as stable doses of nonsteroidal anti-inflammatory drugs (NSAIDS), and prednisone at doses of less than 10 mg/day were continued (Table 1). Patient 10 was also taking a beta-blocker (Corgard). Gold salts, D-pencillamine, or methotrexate were discontinued at least 2 months prior to the study. Patients initially received 6 mg/kg/day of cyclosporine in a single dose. The dose was subsequently adjusted upwards or downwards, based on clinical efficacy or toxicity, with a maximum dose of 8 mg/kg/day. Cyclosporine was administered for a period of 24 weeks, followed by a 12-week washout phase. Renal function was clinically evaluated by monitoring serum creatinine and BUN, and serious nephrotoxicity which required interruption of the protocol was defined as a serum creatinine of greater than 2.0 mg/100 ml or a BUN of greater than 40.0 mg/100 ml.

ASSAYS

Urinary kallikrein excretion, as measured by kallikrein radioimmunoassay, does not appear to show a consistent or significant pattern of diurnal variation in normal individuals (Table 2). This finding made it possible to request that patients collect urine for 12 hours (rather than 24 hr.) in order to enhance compliance. Collections were made at weeks 0, 12, 24, 28, 32 and 36. Urine was stored at 4° C. during the collection period and brought the next day to the Ambulatory Center. An aliquot was removed and frozen at −70° C. for kallikrein radioimmunoassay and the rest was submitted for determination of sodium, potassium, creatinine, and protein. Because the patients were not physically active, creatinine clearance was calculated directly using the data obtained from the 12-hr urine sample; creatinine clearance was also estimated as described by Gates, G. F., *Am. J. Kidney Diseases*, 5:199-205 (1985). Total urinary kallikrein was assayed as described by radioimmunoassay (Spragg, J. et al., *Kidney Internat.*, 28:75-81 (1985), Silver, M. R. et al., *J. Immunol.*, 124:551-1555 (1980)), but with an antiserum that is not specific for epitopes expressed only on the active form of kallikrein (Pinkus, G. S. et al., *Adv. Exp. Med. Biol.*, 156A:367-376 (1983); Pinkus, G. S. et al., *J. Histochem. Cytochem.*, 31:1279-1288 (1983)). Thus, the use of trypsin to fully activate the kallikrein present in the urine (Silver, M. R. et al., *J. Immunol.*, 124:1551-1555 (1980)) was omitted. All samples were assayed in duplicate or triplicate and kallikrein concentrations were determined with a standard curve obtained with highly purified human urinary kallikrein (ole-MoiYoi O. et al., *Proc. Natl. Acad. Sci. USA*, 76:3121-3125 (1979)) quantified by amino acid analysis. Internal standards of highly purified kallikrein were recovered at a mean of 108%. To compare the results obtained with those previously reported (Spragg, J. et al., *Kidney Internat.*, 28:75-81 (1985)), the results are expressed as ug of total kallikrein excreted/24 hrs. Data for groups of samples are presented as the mean ± the standard deviation (S.D.). Paired or unpaired two-tailed t tests were used to compare samples obtained at different times, points, or from different patient groups, respectively. Linear regression analysis was assisted by the Clinfo Data Computer Center at the Brigham and Women's Hospital.

RESULTS

Figure 1:
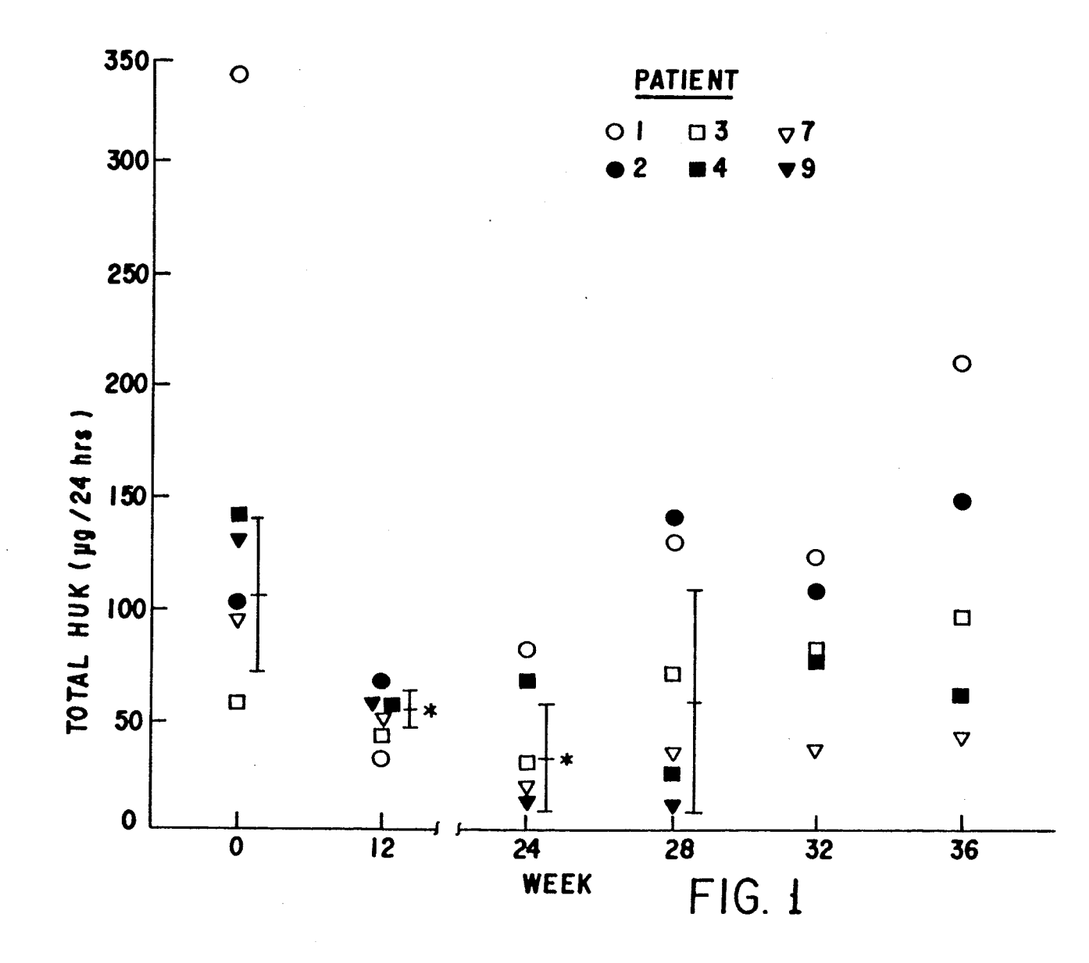
Figure 2:
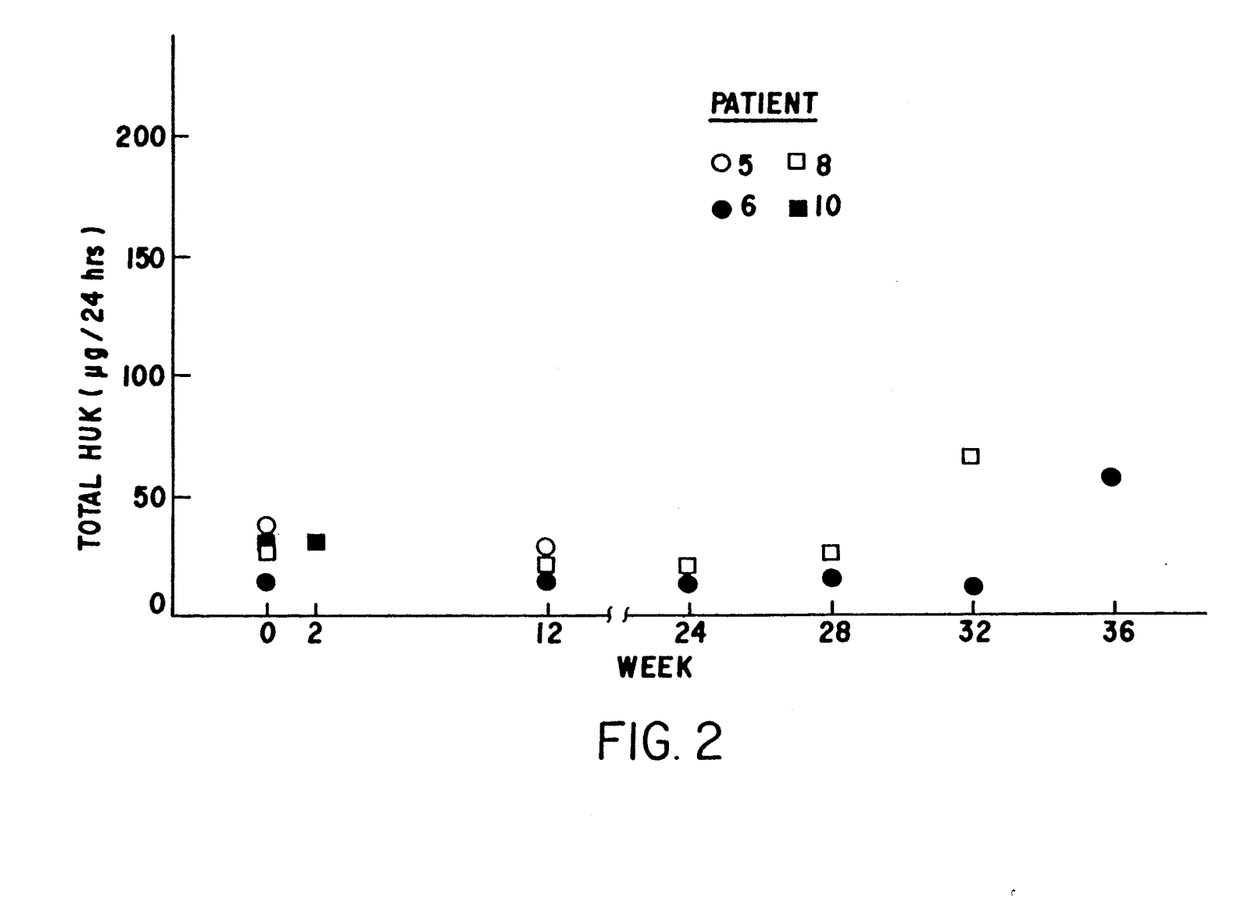
FIG. 2 is a graphic representation of the effects of cyclosporine administration on urinary kallikrein excretion rates in rheumatoid arthritis patients who had significantly depressed HUK excretion baseline levels. The drug schedule was as described in FIG. 1. Patients 5 and 10 were dropped from the study.

Baseline (week 0) urinary kallikrein excretion rates for the ten rheumatoid arthritis patients initially enrolled in the cyclosporine trial were, with the exception of one value, segregated into two separate groups (FIGS. 1 and 2). Five individuals (patients 2, 3, 4, 7 and 9) had a mean baseline kallikrein excretion rate of 106.6,±34.06 ug/24 hr. This was similar to that of the previously examined normal population of 113.68±8.39 (SEM) ug/24 hr. (Spragg, et al., *Kidney Int.* 28:75-81 (1985)). Four other patients (numbers 5, 6, 8 and 10) had mean baseline kallikrein excretion rates of 28.25,±10.11 ug/24 hrs (FIG. 2). The remaining participant (patient 1) had a baseline total kallikrein excretion rate which was three-fold higher than the normal mean (FIG. 1). There was no apparent relationship between baseline kallikrein excretion rates, (FIGS. 1 and 2) sodium excretion, and baseline medication for either rheumatoid arthritis or concomitant medical conditions (Table 1). Baseline serum creatinine levels and BUN levels were within the normal range (0.6 to 1.2 mg/100 ml and 8 to 24 mg/100 ml, respectively) for all ten patients (Table 3) except for low BUN in patient 1.

Three months after cyclosporine therapy was begun, the kallikrein excretion rates of all nine continuing participants had declined (FIGS. 1 and 2). In the group of patients with baseline kallikrein excretion within the normal range (FIG. 1), the mean total kallikrein excretion had fallen from 106.6,±34.06, to 56.6,±8.91, ug/24 hr ($p<0.01$ compared to the baseline values), and the percent decrease in excretion ranged from 21% to 59% (mean=43%). By 6 months after initiation of drug therapy, the mean HUK excretion for this group was 34.5,±24.69, ug/24 hr ($p<0.005$ compared to baseline). Of the five patients in this group, only one (number 4) developed a significant nephrotoxic response to cyclosporine administration as indicated by a serum creatinine of 2.0 mg/100 ml at week 16 (285% of baseline) compared to a mean of 1.2±0.22 mg/100 ml (175±26.6 percent of baseline) at week 16 for the other patients in this group. After cyclosporine was stopped for 1 week, patient 4 had a serum creatinine of 1.3 mg/100 ml. His blood presure had risen from a baseline of 130/80 to 140/100 mm Hg at 16 weeks and hydrochlorothiazide treatment was initiated.

The significantly elevated baseline kallikrein excretion rate seen in patient 1 fell to 11% of the control value by week 12 (FIG. 1) in association with a significant nephrotoxic response as defined by a serum creatinine of 2.6 mg/100 ml (370% of baseline) (Table 3). She required an increased dose of hydrochlorothiazide beginning at week 12 since her blood pressure had risen from 130/85 at baseline to 170/100. By week 36, two months after cyclosporine was stopped, her kallikrein excretion rate had returned to 63% of the high baseline value (FIG. 1). While siginificant nephrotoxic responses as defined by serum creatinines > 2 mg/100 ml occurred in two of the six patients depicted in FIG. 1, the other four manifested mild renal insufficiency by week 12 as indicated by an increase in serum creatinine to more than 120% of their entry values. None of the patients depicted in FIG. 1 experienced BUN levels in the defined toxic range (>40 mg/100 ml) at any time during the study, although increases over baseline ranging from 36% to 400% were observed at 12 weeks. All patients in this group were able to complete the 36-week protocol.

The group of four patients with low baseline kallikrein excretion rates (FIG. 2) included the two individuals in whom cyclosporine administration was terminated. Patient 10 demonstrated significant nephrotoxicity by week 4 as indicated by a BUN of 45 mg/100 ml. While patient 5 had cyclosporine therapy interrupted from weeks 6 to 8 and then discontinued at week 12 primarily because of an elevated SGPT, her early increase in BUN (35 mg/100 ml at week 4 compared to 11 mg/100 ml at week 2) was significantly greater than that of the eight patients who completed the trial (mean BUN = 19.5 ± 3.85 mg/100 ml at week 4) and she likely would have met the study criteria for nephrotoxicity had cyclosporine been continued. A nephrotoxic response was also seen in patient 8, who had BUN levels of 42 at weeks 12 and 16 (280% of baseline) (Table 3). After cyclosporine was stopped for one month, her BUN dropped to 26 mg/100 ml. Hydrochlorothiazide was begun at week 12 to control her blood pressure, which had risen from 160/80 to 150/95. None of the patients with low baseline kallikrein excretion rates experienced an elevation in their serum creatinine levels into the defined toxic range (>2 mg/100 ml) at any time during the study, although increases of 150%, 128% and 188% were seen at week 12. Cyclosporine administration to patients 5, 6 and 8 produced modest reductions in urinary kallikrein excretion by week 12, which ranged from 74% to 93% of the abnormally low baseline values; statistical significance was not determined because of the limited number of values.

In addition to the significant nephrotoxic responses seen in a limited number of patients, all individuals developed mild renal insufficiency, as indicated by an increase in serum creatinine to more than 20% of their entry values. Creatinine clearance rates (CCr in Table 3), either calculated directly or estimated from the serum creatinine, correlated moderately well with each other at all time points ($r^2$ ranged from 0.70 to 0.82). In six of nine patients creatinine clearance was less than 75% of the control value by week 12, and was less than 75% of the control value in all patients by week 24 (Table 3). There was no significant correlation between kallikrein excretion and serum creatinine, creatinine clearance, urinary sodium, or urinary potassium, either before or during the study, except for a moderately good relationship between kallikrein and ion excretion at week 28.

In the limited number of patients who were available for study, it is apparent that those who had baseline kallikrein excretion rates within normal limits had significantly depressed rates when examined three and six months after initiation of cyclosporine therapy (FIG. 1). Since their steroidal and non-steroidal antiinflammatory drugs and concomitant medications had been stabilized one month prior to the study and continued throughout the study period, the altered kallikrein excretion represents the effect of cyclosporine and not simply that of the other therapeutic agents. Quantitative recovery of kallikrein added to urine samples indicates that a substance that might interfere with the radioimmunoassay is not responsible for the depressed values. In spite of the significant decrease in kallikrein excretion during cyclosporine therapy, no one in this group had to withdraw from the study and only one individual experienced a significant nephrotoxic response. While all patients in this group have yet to complete the protocol, the initial data indicate that this effect of cyclosporine is generally reversible (FIG. 1).

The group of four patients with significantly depressed baseline kallikrein excretion rates exhibited modest decrements in kallikrein excretion during cyclosporine administration which reversed after termination of the drug (FIG. 2). The low baseline kallikren levels compared to those found in the group discussed above cannot be attributed to a difference in concomitant medications, to any apparent differences in prior therapy with plaquenil, gold, gold salts, D-penicillamine, or methotrexate or to excretion of a substance interfering with the radioimmunoassay. Three of the four patients in this group developed serious nephrotoxic reactions to cyclosporine and two of them had to be dropped from the study.

The above data suggest that baseline kallikrein excretion, as a reflection of functional tubular mass (Spragg, J. et al., *Kidney Internat.*, 28:75-81 (1985)) is also a useful predictor of nephrotoxic responses to cyclosporine administration. Although the excretion of this distal tubule enzyme was diminished during the drug therapy in all patients studied, the incidence of toxic response was clearly greater in the group with low baseline levels (¾) than in the group with normal baseline levels (1/5). In contrast, baseline levels of glomerular function, as indicated by serum creatinine and BUN values, were within normal limits for all patients enrolled in the study.

In addition, the data indicate that the diminished kallikrein excretion rates observed in renal transplant recipients (Spragg, J. et al., *Kidney Internat.*, 28:75-81 (1985)) reflect not only rejection reactions and possibly altered synthetic or secretory activity in the denervated kidney, but also indicate a renal response to cyclosporine itself.

EXAMPLE

A low-dose (3 mg/kg/day) open extension study followed the initial trial, in which kallikrein excretion was determined monthly. Episodes in which kallikrein excretion decreased by 49 ± 15% over a one-month interval preceded any increase in serum creatinine by one to four months.

During the first phase of the trial, described in the preceding Example, patients initially received 6 mg/kg/day of cyclosporine in a single dose. The dose was subsequently adjusted upward, on the basis of a need for greater clinical efficacy, with a maximum dose of 8 mg/kg/day; it was adjusted downward, temporarily interrupted, or discontinued if toxicity developed. During the first phase of the study (phase one) cyclosporine was administered for 24 weeks, followed by a 12-week washout period. Renal function was evaluated by serum creatinine and BUN, and serious nephrotoxicity that required interruption of the protocol was arbitrarily defined as a serum creatinine greater than or equal to 2.0 mg/100 ml or a BUN greater than or equal to 40.0 mg/100 ml.

At week 36, 7 of the 10 patients (1,2,3,4,6,7,8,9) entered an extension protocol (phase two) and initially received 3 mg/kg/day of cyclosporine in two doses. Two patients, numbers 4 and 8, discontinued the agent at three and six months, respectively, and five completed at least nine months on the extension protocol. Nephrotoxicity was monitored as described. The cyclosporine dose was increased to 4 mg/kg/day if the lower dose was ineffective and was decreased to 1.5 or 2 mg/kg/day or temporarily interrupted if toxicity developed.

The temporal relationship between decreased kallikrein excretion and increased serum creatinine was assessed by monthly sampling while patients received a reduced dose of cyclosporine (phase two). Of the seven patients participating in phase two, five patients had episodes during which kallikrein excretion decreased by 49±15% over a one-month interval with no increment in serum creatinine (Table 4). When the observation period was extended to two months, the percent decrease in kallikrein from the beginning of the episodes was 72±13% and increments in serum creatinine were associated with three of the episodes. When the observation period was extended to four months, serum creatinine elevations were seen in the rest of the patients in association with a maintained depression in kallikrein excretion. The occurrence of these episodes was not particularly associated with low or normal baseline kallikrein excretion rates.

Discussion

During the second phase of the present study, reduced doses of cyclosporine also led to episodes of markedly reduced kallikrein excretion, which occurred at least one month before elevations in serum creatinine levels were seen (Table 4). This temporal dissociation of decreased kallikrein excretion and elevated serum creatinines may be due both to more frequent sampling and to the lower cyclosporine doses used during phase two. At the creatinine levels present in these patients (0.7 to 1.1 mg/100 ml), small increments in serum creatinine, often within the range of laboratory error, reflect substantial losses of filtering nephrons. Rose, B. D., "Clinical assessment of renal function," in B. D. Rose, ed., *Pathophysiology of Renal Disease.* 1st Edition, McGraw Hill, pp. 1-30 (1981).

While the mechanism by which cyclosporine affects renal kallikrein synthesis and/or excretion remains to be elucidated, the use of this drug in patients other than renal allograft recipients is in trial or contemplated. Thus the determination of excretion rates of this enzyme is useful in evaluating nephrotoxicity and has predictive value in identifying individuals, other than renal allograft recipients, who are at greater risk for developing nephrotoxic reactions to cyclosporine.

Thus it may be seen that the present invention provides a novel method for detecting and evaluating nephrotoxicity in response to potentially nephrotoxic agents such as cyclosporine, aminoglycoside antibiotics, analgesics such as phenacetin, and non-steroidal antiinflammatory agents such as aspirin, as well as a multitude of nephrotoxic chemicals found in our environment. While monitoring serum creatinine provides information relating to filtration function, and monitoring BUN reflects both glomerular filtration and sodium-associated tubular readsorption, kallikrein excretion provides a measure of the synthetic and secretory function of the distal nephron, which may be significantly altered in certain circumstances where filtration/readsorption is within normal limits.

In addition to the homogeneous phase radioimmunoassay described above, many variations of radioimmunoassay may be used as well. Typically, such radioimmunoassays include heterogeneous or solid phase radioimmunoassay, single antibody methods or "double" antibody methods, and direct (forward) or reverse sandwich assays. A typical solid phase system includes antibody covalently coupled to an insoluble support so that both the antibody and the bound complex after incubation can be readily separated from the soluble free fraction. A wide variety of solid phase supports have been described, which include particles of dexstran, cellulose, continuous surfaces such as polystyrene or polypropylene disks, walls of plastic tubes, glass disks, glass particles, and the like. Particular solid phases are widely used for a variety of different assays and are included in the present invention. Another known method for immobilization involves the biotin-avidin complex formation.

Enzyme immunoassays may be used as well. In this technique, enzymes are applied labels on antigen or antibodies for identification and localization of the immunoreactants. Any method in which the extent of binding of enzyme-labeled antigen, or enzyme labeled-antibody to its immunoreactant is measured, is included in this invention. Enzyme immunoassays may be classified as homogeneous or heterogeneous, depending on whether the labeled reagent behaves differently or identically whether or not it is bound to specific counterparts in the immunoreaction, in which therefore it may or may not require physical separation of the reactants into two fractions.

Another immunoassay method in the present invention is the latex agglutination method In this method, latex particles are coated with antigen and incubated with a high affinity hybridomally produced antibody. Inhibition of agglutination will recur when a sample of physiological fluid containing the antigen is incubated with this mixture. The inhibition of agglutination can either be followed with a counter or by infrared absorption techniques.

TABLE 1

Characteristics of rheumatoid arthritis patients enrolled in the cyclosporine (CsA) protocol

| | | Age | Duration (yrs) | | NSAIDS | Baseline drugs | | CsA dose when urine collected at week: (mg/kg/day) | | |
|---|---|---|---|---|---|---|---|---|---|---|
| Patient | Sex | (yrs) | disease | therapy | (mg/day) | Prednisone (mg) | Other (mg/day) | 12 | 24 | 28 |
| 1 | F | 54 | 17 | 16 | 4500$^a$ | — | Hydrochlorothiazide, 50 | 6 | 0 | 0 |
| 2 | F | 50 | 7 | 7 | 20$^b$ | 10/day | | 6 | 8 | 0 |
| 3 | F | 61 | 4.5 | 4.5 | 2400$^a$ | — | | 6 | 6 | 0 |
| 4 | M | 36 | 12 | 12 | 4800$^a$ | 10 q.o.d. | | 6 | 6 | 0 |
| 5 | F | 59 | 8 | 8 | 1800$^a$ | 5/day | | 0 | — | — |
| 6 | F | 32 | 9 | 8 | — | 5/day | | 6 | 8 | 0 |
| 7 | F | 50 | 3 | 3 | 1000$^c$ | 10 q.o.d. | Ranitidine, 150 | 6 | 6 | 0 |
| 8 | F | 69 | 12 | 12 | 1000$^c$ | 10 q.o.d. | | 6 | 4 | 0 |
| 9 | M | 66 | | | | 7.5/day | | 6 | 6 | 0 |
| 10 | F | 66 | 16 | 5 | 20$^b$ | 10/day | Hydrochlorothiazide, 50 | 6 | — | — |

TABLE 1-continued

Characteristics of rheumatoid arthritis patients enrolled in the cyclosporine (CsA) protocol

| Patient | Sex | Age (yrs) | Duration (yrs) disease | NSAIDS therapy (mg/day) | Baseline drugs Prednisone (mg) | Other (mg/day) | CsA dose when urine collected at week: (mg/kg/day) | | |
|---|---|---|---|---|---|---|---|---|---|
| | | | | | | | 12 | 24 | 28 |
| | | | | | | Corgard, 80 | | | | aspirin
Feldene
Naprosyn

TABLE 2

Twenty-four hour kallikrein excretion pattern in normal volunteers

| Donor | Total kallikrein/collection period (ug) | | | |
|---|---|---|---|---|
| | 6 A.M. to Noon | Noon to 6 P.M. | 6 P.M. to Midnight | Midnight to 6 A.M. |
| 1 | 50 | 50 | 35 | 38 |
| 2 | 20 | 20 | 20 | 14 |
| | 19 | 19 | 19 | 17 |
| 3 | 70 | 68 | 79 | 75 |
| 4 | 105 | 104 | 104 | 120 |
| 5 | 21 | 11 | 16 | 11 |
| 6 | 21 | 18 | 19 | 19 |
| 7 | 44 | 50 | 43 | 40 |
| 8 | 28 | 46 | 38 | 30 |
| 9 | 37 | 36 | 28 | 27 |
| 10 | 50 | 41 | 54 | 54 |
| Mean = | 42.27 | 42.09 | 41.36 | 40.45 |
| S.D. | 26.46 | 26.93 | 27.99 | 32.52 |

No mean value was significantly different from any other

TABLE 3

Renal responses to cyclosporine therapy in patients with rheumatoid arthritis

| Parameter Week | Serum creatinine (mg/100 ml) | | | | CCr (ml/min) | | | | BUN (mg/100 ml) | | | | Blood pressure (mm Hg) | | | |
|---|---|---|---|---|---|---|---|---|---|---|---|---|---|---|---|---|
| | 0 | 12 | 24 | 28 | 0 | 12 | 24 | 28 | 0 | 12 | 24 | 28 | 0 | 12 | 24 | 28 |
| Patients FIG. 1 | | | | | | | | | | | | | | | | |
| 1 | 0.7 | 2.6 | 1.2 | 1.0 | 82 | 13 | 50 | 52 | 6 | 31 | 19 | 11 | 130/85 | 170/100 | 170/90 | 130/85 |
| 2 | 0.7 | 1.2 | 1.4 | 0.8 | 156 | 101 | ND | 154 | 15 | 28 | 24 | 15 | 150/80 | 140/85 | 140/85 | 150/85 |
| 3 | 0.5 | 0.6 | 0.8 | 0.8 | 107 | 102 | 59 | 94 | 14 | 19 | 15 | 13 | 130/80 | 140/80 | 140/70 | 130/80 |
| 4 | 0.7 | 1.5 | ND | 1.0 | 152 | 98 | ND | 174 | 15 | 33 | 14 | 15 | 130/80 | 140/95 | 130/85 | 130/85 |
| 7 | 0.8 | 1.3 | 1.3 | 1.1 | 96 | 65 | 51 | 82 | 15 | 34 | 24 | 17 | 110/80 | 140/85 | 150/80 | 150/80 |
| 9 | 0.7 | 1.1 | 1.9 | 1.0 | 167 | 99 | 68 | 106 | 17 | 30 | 31 | 18 | 130/70 | 160/90 | 145/90 | 130/80 |
| Patients FIG. 2 | | | | | | | | | | | | | | | | |
| 5 | 0.8 | 1.2 | | | 95 | 83 | | | ND (35 at week 4) | | | | 150/90 | 150/105 at week 4) | | |
| 6 | 0.7 | 0.9 | 1.1 | 0.7 | 114 | 87 | 64 | 120 | ND | 23 | 27 | 11 | 120/70 | 130/85 | 150/95 | 130/80 |
| 8 | 0.8 | 1.5 | 1.2 | 1.1 | 59 | 26 | 44 | 76 | 15 | 42 | 27 | 18 | 160/80 | 150/95 | 160/80 | 145/85 |
| 10 | 1.2 (1.5 at week 4) | | | | 59 | | | | 22 (45 at week 4) | | | | 150/100 | | | |

ND = not determined

TABLE 4

Temporal relationship between decreased kallikrein (HUK) excretion and increased serum creatinine (Ser Cr) during phase two

| Patient* | Changes observed over 1 month | | Changes observed over 2 months | |
|---|---|---|---|---|
| | HUK % decrease | Ser Cr % increase | HUK % decrease | Ser Cr % increase |
| 1 (1) | 72 | 0 | 60 | 50 |
| 1 (2) | 49 | 0 | 80 | 0 |
| 2 | 38 | 0 | 56 | 23 |
| 6 | 34 | 0 | 92 | 0 |
| 7 | 38 | 0 | 75 | 0 |
| 9 | 60 | 0 | 70 | 8 |
| Mean | 49 ± 15% | 0 | 72 ± 13% | 13 ± 20% |

*Two episodes of decreased kallikrein excretion were observed in patient 1.

Having now fully described this invention, it will now become readily apparent to one skilled in the art that many changes and modifications may be made thereto without affecting the spirit or scope thereof.

We claim:

1. A method for evaluating the potential nephrotoxic effect of a composition administered to a patient other than a renal allograft recipient, said method comprising:
   (a) obtaining a biological sample of urine from a patient before administering said composition;
   (b) mixing said sample of step (a) with a monospecific antibody for urokallikrein/kallikrein;
   (c) measuring the amount of kallikrein in said sample of step (b) bound to said antibody to determine a baseline value;
   (d) administering said composition to said patient;
   (e) obtaining a biological sample of urine from said patient to whom said composition has been administered;
   (f) mixing said sample of step (e) with a monospecific antibody for urokallikrein/kallikrein;
   (g) measuring the amount of kallikrein in said sample of step (f) bound to said antibody; and
   (h) comparing the result obtained in step (g) to said patient's baseline kallikrein values;

wherein decreased kallikrein content relative to said baseline value is indicative of nephrotoxic effect.

2. The method of claim 1, wherein said label is a radiolabel.

3. The method according to claim 2, wherein said measuring step (c) comprises:
   (i) adding a quantity of labeled urokallikrein to said sample and said antibody;
   (ii) incubating for a time sufficient for the formation of an antibody urokallikrein/kallikrein complex;
   (iii) separating bound labeled urokallikrein from unbound labeled urokallikrein;
   (iv) determining the amount of bound or unbound labeled urokallikrein; and, (v) comparing the results obtained to known standard measurements to determine the amount of kallikrein in said sample.

4. The method according to claim 1, wherein said antibody recognizes both the active and trypsin-activatable forms of urokallikrein.

5. The method according to claim 1, wherein said antibody is specific for the active site of urokallikrein.

6. The method according to claim 1, wherein said antibody is a monoclonal antibody.

7. The method according to claim 1, wherein said measuring step (c) comprises:
(i) adding a quantity of labeled urokallikrein to said sample and said antibody;
(ii) incubating for a time sufficient for the formation of an antibody-urokallikrein/kallikrein complex;
(iii) separating bound labelled urokallikrein from unbound labeled urokallikrein;
(iv) determining the amount of bound or unbound labeled urokallikrein; and,
(v) comparing the results obtained to standard measurements to determine the amount of kallikrein in said sample.

8. The method according to claim 1, wherein said labeled urokallikrein is labeled with a label selected from the group consisting of a radiolabel, a luminescent label, a chemiluminescent label, an enzyme label, and a free radical label.

9. The method of claim 1, wherein steps (a)-(d) are repeated more than one time to monitor the potential nephrotoxic effect of said composition.

10. A method for predicting whether a non-renal allograft patient is prone to experience nephrotoxicity, said method comprising:
(a) obtaining a biological sample of urine from an individual suspected of developing a neophrotixic reaction;
(b) mixing said sample of step (a) with a monospecific antibody for urokallikrein/kallikrein;
(c) measuring the amount of kallikrein in said sample of step (b) bound to said antibody; and
(d) comparing the result obtained in step (c) to a normal baseline standard value;
wherein decreased kallikrein content relative to said baseline value is indicative of nephrotoxicity.

11. The method according to claim 10, wherein said antibody recognizes both the active and trypsin activatable forms of urokallikrein.

12. The method according to claim 10, wherein said antibody is specific for the active site of urokallikrein.

13. The method according to claim 10, wherein said antibody is a monoclonal antibody.

14. The method according to claim 10, wherein said labeled urokallikrein is labeled with a label selected from the group consisting of a radiolabel, a luminescent label, a chemiluminescent label, an enzyme label, and a free radical label.

15. The method of claim 10, wherein said label is a radiolabel.

16. A method for predicting an increase in serum creatinine in a non-renal allograft patient undergoing nephrotoxic therapy, said method comprising:
(a) obtaining b biological sample for a patient preparing to undergo nephrotoxic therapy;
(b) mixing said sample of step (a) with a monospecific antibody for urokallikrein/kallikrein;
(c) measuring the amount of kallikrein in said sample of step (b) bound to said antibody to determine a baseline value;
(d) obtaining a biological sample of urine from said patient undergoing nephrotoxic therapy and suspected of developing a nephrotoxic reaction;
(e) mixing said sample of step (d) with a monospecific antibody for urokallikrein/kallikrein;
(f) measuring the amount of kallikrein in said sample of step (e) bound to set antibody; and
(g) comparing the result obtained in step (f) to said patient's baseline kallikrein value.

17. The method according to claim 16, wherein said antibody recognizes both the active and trypsin-activatable forms of urokallikrein.

18. The method according to claim 16, wherein said antibody is specific for the active site of urokallikrein.

19. The method according to claim 16, wherein said antibody is a monoclonal antibody.

20. The method according to claim 16, wherein said measuring step (c) comprises:
(i) adding a quantity of labeled urokallikrein to said sample and said antibody;
(ii) incubating for a time sufficient for the formation of an antibody-urokallikrein/kallikrein complex;
(iii) separating bound labeled urokallikrein from unbound labeled urokallikrein;
(iv) determining the amount of bound or unbound labeled urokallikrein; and,
(v) comparing the results obtained to standard measurements to determine the amount of kallikrein in said sample.

21. The method according to claim 16, wherein said labeled urokallikrein is labeled with a label selected from the group consisting of a radiolabel, a luminescent label, a chemiluminescent label, an enzyme label, and a free radical label.

22. The method according to claim 16, wherein said label is a radiolabel.

23. A method for determining the potential nephrotoxic effect of a composition, wherein said composition is selected from the group consisting of cyclosporine, aminoglycoside antibiotics, analgesics, non-steroidal anti-inflammatories, and environmental contaminants, said method comprising:
(a) obtaining a biological sample of urine from a non-renal allograft patient;
(b) mixing said sample of step (a) with a monospecific antibody for urokallikrein/kallikrein;
(c) measuring the amount of kallikrein in said sample of step (b) bound to said antibody to determine a baseline value;
(d) administering said composition to said patient;
(e) obtaining a biological sample of urine from said patient suspected of developing a nephrotoxic reaction to said composition;
(f) mixing said composition of step (e) with a monospecific antibody for urokallikrein/kallikrein;
(g) measuring the amount of kallikrein in said sample of step (f) bound to set antibody; and
(h) comparing the result obtained in step (g) to said patient's baseline kallikrein value.

24. The method of claim 23, wherein said composition is cyclosporine.

* * * * *

UNITED STATES PATENT AND TRADEMARK OFFICE
CERTIFICATE OF CORRECTION

PATENT NO. : 5,045,452
DATED : September 3, 1991
INVENTOR(S) : Spragg, et al

It is certified that error appears in the above-indentified patent and that said Letters Patent is hereby corrected as shown below:

Column 1, beneath "Method For Evaluating Nephrotoxicity" insert --This invention was made with government support under Grant Nos. HL22939 and HL35959 awarded by the National Institutes of Health. The government has certain rights in the invention--.

Signed and Sealed this

Fifth Day of April, 1994

Attest:

BRUCE LEHMAN

*Attesting Officer*  *Commissioner of Patents and Trademarks*